US012635714B2

(12) United States Patent
Pan et al.

(10) Patent No.: US 12,635,714 B2
(45) Date of Patent: May 26, 2026

(54) COMPOSITIONS AND METHODS FOR PROVIDING A HEALTH BENEFIT TO A GROWING ANIMAL

(71) Applicant: Société des Produits Nestlé S.A., Vevey (CH)

(72) Inventors: Yuanlong Pan, Chesterfield, MO (US); Hui Xu, Chesterfield, MO (US); Sandeep Bhatnagar, Ballwin, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 160 days.

(21) Appl. No.: 17/101,485

(22) Filed: Nov. 23, 2020

(65) Prior Publication Data

US 2021/0186054 A1 Jun. 24, 2021

Related U.S. Application Data

(60) Provisional application No. 62/950,672, filed on Dec. 19, 2019.

(51) Int. Cl.

| | |
|---|---|
| *A23K 20/105* | (2016.01) |
| *A23K 20/142* | (2016.01) |
| *A23K 20/158* | (2016.01) |
| *A23K 20/163* | (2016.01) |
| *A23K 20/174* | (2016.01) |
| *A23K 50/40* | (2016.01) |
| *A23L 33/12* | (2016.01) |
| *A23L 33/15* | (2016.01) |
| *A61K 31/14* | (2006.01) |
| *A61K 31/197* | (2006.01) |
| *A61K 31/202* | (2006.01) |
| *A61K 31/355* | (2006.01) |
| *A61K 31/375* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |

(52) U.S. Cl.
CPC .......... *A23K 20/105* (2016.05); *A23K 20/142* (2016.05); *A23K 20/158* (2016.05); *A23K 20/163* (2016.05); *A23K 20/174* (2016.05); *A23K 50/40* (2016.05); *A23L 33/12* (2016.08); *A23L 33/15* (2016.08); *A61K 31/14* (2013.01); *A61K 31/197* (2013.01); *A61K 31/202* (2013.01); *A61K 31/355* (2013.01); *A61K 31/375* (2013.01); *A61K 31/4415* (2013.01); *A61K 31/455* (2013.01); *A61K 31/51* (2013.01); *A61K 31/519* (2013.01); *A61K 31/525* (2013.01)

(58) Field of Classification Search
CPC .. A23K 20/105; A23K 20/142; A23K 20/158; A23K 20/163; A23K 20/174; A23K 50/40; A23L 33/15; A23L 33/12; A61K 31/197; A61K 31/14; A61K 31/525; A61K 31/455; A61K 31/51; A61K 31/4415; A61K 31/519; A61K 31/355; A61K 31/375; A61K 31/202
See application file for complete search history.

(56) References Cited

U.S. PATENT DOCUMENTS

| | | |
|---|---|---|
| 5,952,033 A | 9/1999 | Anantharaman |
| 5,955,102 A | 9/1999 | Gorenbein et al. |
| 5,968,569 A | 10/1999 | Cavadini |
| 6,929,793 B2 | 8/2005 | Spivey-Krobath et al. |
| 7,189,390 B2 | 3/2007 | Zink et al. |
| 8,496,981 B2 | 7/2013 | Zicker et al. |
| 9,463,167 B2 | 10/2016 | Nolan et al. |
| 2006/0158611 A1 | 7/2006 | Piers et al. |
| 2014/0066747 A1 | 3/2014 | Fortier et al. |

FOREIGN PATENT DOCUMENTS

| | | | |
|---|---|---|---|
| CN | 101686712 A | 3/2010 | |
| CN | 106692187 | 5/2017 | |
| CN | 107708446 A | 2/2018 | |
| CN | 109222086 | 1/2019 | |
| EP | 1143806 | 10/2001 | |
| EP | 1213970 | 6/2002 | |
| EP | 1296565 | 4/2003 | |
| EP | 1482811 | 12/2004 | |
| EP | 3388061 A1 | 10/2018 | |
| JP | 2019534853 A | 12/2019 | |
| RU | 2507742 C2 | 2/2014 | |
| RU | 2694064 C1 | 7/2019 | |
| WO | WO-0000043 A1 * | 1/2000 | .............. A23L 33/11 |
| WO | 2005032271 A1 | 4/2005 | |
| WO | WO 2007/128461 | * 11/2007 | |
| WO | 107708446 | * 2/2018 | |

OTHER PUBLICATIONS

Zheleznyak et al. (IOVS (2013) 54(5) 3157-3165).*
Hernandez et al. (2016) https://doi.org/10.1371/journal.pone.0148436.*
https://www.collinsdictionary.com/US/dictionary/english/glare.*
https://www.merriam-webster.com/dictionary/photopic.*
"Meat Flavor Complete Kitten Food", Mintel, Record Id 6266339, Jan. 17, 2019, pp. 1-3, XP055774838.

(Continued)

*Primary Examiner* — Shirley V Gembeh

(57) ABSTRACT

The present disclosure provides compositions and methods for providing a health benefit to a growing animal comprising administering a food composition to the animal, wherein the food composition includes a brain development blend. The brain development blend generally comprises DHA, EPA, taurine, choline, thiamine, riboflavin, pantothenic acid, niacin, pyridoxine, vitamin B12, and folic acid.

14 Claims, No Drawings

(56) References Cited

OTHER PUBLICATIONS

"Kitten Food with Chicken", Mintel, Record Id 3585761, Mar. 15, 2016, pp. 1-3, XP055774840.

"Complete Premium Kitten Food", Mintel, Record Id 3520367, Nov. 3, 2015, pp. 1-5, XP055774841.

"Dry Food with Chicken for Puppies", Mintel, Record Id 6919483, Oct. 4, 2019, pp. 1-3, XP055774806.

International Search Report and Written Opinion to Appl. No. PCT/IB2020/061047 dated Feb. 12, 2021.

Ushakov, "Explanatory Dictionary of the Modern Russian Language", 2014, p. 245.

Chinese Office Action for Appl No. 202080086257.7 dated Jul. 7, 2023, 7 pages.

Japanese Office Action for Appl No. 2022-534790 dated Jul. 16, 2024, 5 pages.

Russian Office Action for Appl No. 2022118267/10 dated Aug. 2, 2024, 9 pages.

* cited by examiner

COMPOSITIONS AND METHODS FOR PROVIDING A HEALTH BENEFIT TO A GROWING ANIMAL

CROSS REFERENCE TO RELATED APPLICATION

This application claims priority to U.S. Provisional Application Ser. No. 62/950,672 filed Dec. 19, 2019, the disclosure of which is incorporated in its entirety herein by this reference.

BACKGROUND

Generally, dog and cat foods include nutrients sufficient for the animal to maintain general health. However, a number of commercially available dog and cat foods have been modified to address many different nutritional needs. For example, veterinary channel diets have been designed to address renal issues, cognitive issues, heart health, overweight animals, allergies, skin conditions, etc. Additionally, formulations have been designed for different breed types, sizes and life stages. For examples, some diets are designed for growing animals, adult animals, senior animals, or even super senior animals. Despite the array of pet food products, the need remains for the development of innovative formulations using ingredients and nutrients designed to enhance the development of growing animals.

SUMMARY

In one embodiment, a method for providing a health benefit to a growing animal can comprise administering to the animal a food composition containing a brain development blend. The food composition can be administered in an amount to provide from about 10 mg/day to about 3000 mg/day docosahexaenoic acid (DHA), from about 10 mg/day to about 3000 mg/day eicosapentaenoic acid (EPA), from about 50 mg/day to about 2000 mg/day taurine, from about 50 mg/day to about 2000 mg/day choline, from about 0.1 mg/day to about 50 mg/day thiamine, from about 0.1 mg/day to about 50 mg/day riboflavin, from about 0.1 mg/day to about 100 mg/day pantothenic acid, from about 0.1 mg/day to about 250 mg/day niacin, from about 0.1 mg/day to about 50 mg/day pyridoxine, from about 0.1 $\mu$g/day to about 1000 $\mu$g/day vitamin B12, and from about 0.01 mg/day to about 15 mg/day folic acid. The health benefit can be selected from the group consisting of enhanced brain growth and development, increased trainability, increased episodic learning, increased episodic memory, reduced spherical aberration of the eye, enhanced photopic vision, and combinations thereof.

In another embodiment, a food composition for a growing animal can comprise a brain development blend. The brain development blend can comprise from about 5% to about 35% DHA, from about 5% to about 35% EPA, from about 5% to about 35% taurine, from about 5% to about 40% choline, from about 0.01% to about 5% thiamine, from about 0.01% to about 5% riboflavin, from about 0.01% to about 5% pantothenic acid, from about 0.1% to about 5% niacin, from about 0.01% to about 5% pyridoxine, from about 0.0001% to about 1% vitamin B12, and from about 0.001% to about 1% folic acid. Generally, the food composition contains an effective amount of the brain development blend sufficient to provide a health benefit selected from the group consisting of enhanced brain growth and development, increased trainability, increased learning, increased memory, reduced spherical aberration of the eye, enhanced photopic vision, and combinations thereof.

Other and further objects, features, and advantages of the invention will be readily apparent to those skilled in the art.

DETAILED DESCRIPTION

Definitions

The term "animal" means any animal that has a need for supporting optimal brain and cognitive development, and good health during growth and development phase of their life stage, including human, avian, bovine, canine, equine, feline, hircine, lupine, murine, ovine, or porcine animals. In one aspect, the animal can be a mammal. In another aspect, the animal can be a companion animal.

The term "companion animal" means domesticated animals such as cats, dogs, rabbits, guinea pigs, ferrets, hamsters, mice, gerbils, horses, cows, goats, sheep, donkeys, pigs, and the like. In one aspect, the companion animal can be a canine. In another aspect, the companion animal can be a feline.

The term "therapeutically effective amount" means an amount of a compound disclosed herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "treating", "treat", and "treatment" embrace both preventative, i.e., prophylactic, and palliative treatment.

The term "health and/or wellness of an animal" means the complete physical, mental, and social well-being of the animal, not merely the absence of disease or infirmity.

The term "in conjunction" means that the food composition, components thereof, or other compositions disclosed herein are administered to an animal (1) together in a single food composition or (2) separately at the same or different frequency using the same or different administration routes at about the same time or periodically. "Periodically" means that the food composition, components thereof, or other compositions are administered on a schedule acceptable for specific compounds or compositions. "About the same time" generally means that the food composition, components thereof, or other compositions are administered at the same time or within about 72 hours of each other.

The term "food" or "food product" or "food composition" means a product or composition that is intended for ingestion by an animal, including a human, and provides nutrition to the animal.

The term "regular basis" means at least monthly administration and, in one aspect, at least weekly administration. More frequent administration or consumption, such as twice or three times weekly, can be performed in certain embodiments. In one aspect, an administration regimen can comprise at least once daily consumption.

The term "single package" means that the components of a kit are physically associated in or with one or more containers and considered a unit for manufacture, distribution, sale, or use. Containers include, but are not limited to, bags, boxes, cartons, bottles, packages such as shrink wrap packages, stapled or otherwise affixed components, or combinations thereof. A single package may be containers of the food compositions, or components thereof, physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain instructions on how to use the kit or safety or technical information about one or more components of a kit.

The term "about" means plus or minus 20% of a numeric value; in one aspect, plus or minus 10%; in another aspect, plus or minus 5%; and in one specific aspect, plus or minus 2%. For example, in one aspect where about is plus or minus 20% of a numeric value, the phrase "from about 10% to about 20%" could include a range from 8% to 24% or 12% to 16%, include any subranges therein.

As used herein, embodiments, aspects, and examples using "comprising" language or other open-ended language can be substituted with "consisting essentially of" and "consisting of" embodiments.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO) as of Jan. 1, 2019.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed. When referring to a food composition, such percentages are of the food composition. When referring to a blend, such percentages are of the blend.

As used herein, ranges are used herein in shorthand, so as to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a supplement", "a method", or "a food" includes a plurality of such "supplements", "methods", or "foods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, certain compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

DETAILED DESCRIPTION

The present methods and compositions are based upon the discovery that specific nutrient blends for growing animals have been found to increase trainability, increase episodic learning, increase episodic memory, reduce spherical aberration of the eye, and enhance photopic vision in the animal.

In one embodiment, a method for providing a health benefit to a growing animal can comprise administering to the animal a food composition containing a brain development brain. The food composition can be administered in an amount to provide from about 10 mg/day to about 3000 mg/day DHA, from about 10 mg/day to about 3000 mg/day EPA, from about 50 mg/day to about 2000 mg/day taurine, from about 50 mg/day to about 2000 mg/day choline, from about 0.1 mg/day to about 50 mg/day thiamine, from about 0.1 mg/day to about 50 mg/day riboflavin, from about 0.1 mg/day to about 100 mg/day pantothenic acid, from about 0.1 mg/day to about 250 mg/day niacin, from about 0.1 mg/day to about 50 mg/day pyridoxine, from about 0.1 µg/day to about 1000 µg/day vitamin B12, and from about 0.01 mg/day to about 15 mg/day folic acid. The health benefit can be selected from the group consisting of enhanced brain growth and development, increased trainability, increased episodic learning, increased episodic memory, reduced spherical aberration of the eye, enhanced photopic vision, and combinations thereof.

In another embodiment, a food composition for a growing animal can comprise a brain development blend. The brain development blend can comprise from about 5% to about 35% DHA, from about 5% to about 35% EPA, from about 5% to about 35% taurine, from about 5% to about 40% choline, from about 0.01% to about 5% thiamine, from about 0.01% to about 5% riboflavin, from about 0.01% to about 5% pantothenic acid, from about 0.1% to about 5% niacin, from about 0.01% to about 5% pyridoxine, from about 0.0001% to about 1% vitamin B12, and from about 0.001% to about 1% folic acid. Generally, the food composition contains an effective amount of the brain development blend sufficient to provide a health benefit selected from the group consisting of enhanced brain growth and development, increased trainability, increased episodic learning, increased episodic memory, reduced spherical aberration of the eye, enhanced photopic vision, and combinations thereof.

As discussed herein, the brain development can be used in various forms such a pet food composition, main meal composition, treats, supplements, and the like. In one embodiment, the food composition can comprise from about 15% to about 70% protein, from about 5% to about 50% carbohydrate, from about 5% to about 40% fat, and the brain development blend.

Generally, the blend generally includes docosahexaenoic acid (DHA), eicosapentaenoic acid (EPA), taurine, choline, thiamine, riboflavin, pantothenic acid, niacin, pyridoxine, vitamin B12, and folic acid. The blend can further comprises vitamin C and vitamin E. Generally, the blend is provided in an effective amount to provide at least one of the health benefits discussed herein. In one aspect, the health benefit can be increased trainability. In another aspect, the health benefit can be increased episodic learning. In still another aspect, the health benefit can be increased episodic memory. In yet another aspect, the health benefit can be reduced spherical aberration of the eye. In still another aspect, the health benefit can be enhanced photopic vision. In yet another aspect, the health benefit can be enhanced brain growth and development.

Generally, DHA can be present in the food composition in an amount to provide a daily dose from about 10 mg/day to about 3000 mg/day. In some aspects, DHA can be administered in amounts of about 100 mg/day to about 1000 mg/day, or even about 140 mg/day to about 500 mg/day. In other embodiments, the DHA can be present in the food composition is an amount ranging from about 100 mg/kg to about 3000 mg/kg, about 1000 mg/kg to about 3000 mg/kg, or even about 1500 mg/kg to about 2500 mg/kg. Additionally, DHA can be calculated as an amount of the brain development blend. As such, DHA can be present in the brain development blend in an amount from about 50 g/kg to about 350 g/kg DHA, about 100 g/kg to about 300 g/kg, or even about 150 g/kg to about 250 g/kg. As a percentage, the DHA can be present as part of the brain development blend in an amount from about 5% to about 35%, about 10% to about 30%, or even about 15% to about 25%.

Generally, EPA can be present in the food composition in an amount to provide a daily dose from about 10 mg/day to about 3000 mg/day. In some aspects, EPA can be administered in amounts of about 100 mg/day to about 1000 mg/day, or even about 140 mg/day to about 500 mg/day. In other embodiments, the EPA can be present in the food composition is an amount ranging from about 100 mg/kg to about 3000 mg/kg, about 1000 mg/kg to about 3000 mg/kg, or even about 1500 mg/kg to about 2500 mg/kg. Additionally, EPA can be calculated as an amount of the brain development blend. As such, EPA can be present in the brain development blend in an amount from about 50 g/kg to about 350 g/kg, about 100 g/kg to about 300 g/kg, or even about 150 g/kg to about 250 g/kg. As a percentage, the EPA can be present as part of the brain development blend in an amount from about 5% to about 35%, about 10% to about 30%, or even about 15% to about 25%.

Generally, taurine can be present in the food composition in an amount to provide a daily dose from about 50 mg/day to about 2000 mg/day. In some aspects, taurine can be administered in amounts of about 100 mg/day to about 1000 mg/day, or even about 150 mg/day to about 600 mg/day. In other embodiments, the taurine can be present in the food composition is an amount ranging from about 100 mg/kg to about 5000 mg/kg, about 1000 mg/kg to about 4000 mg/kg, or even about 1500 mg/kg to about 2500 mg/kg. Additionally, taurine can be calculated as an amount of the brain development blend. As such, taurine can be present in the brain development blend in an amount from about 50 g/kg to about 350 g/kg, about 100 g/kg to about 300 g/kg, or even about 150 g/kg to about 250 g/kg. As a percentage, the taurine can be present as part of the brain development blend in an amount from about 5% to about 35%, about 10% to about 30%, or even about 15% to about 25%.

Generally, choline can be present in the food composition in an amount to provide a daily dose from about 50 mg/day to about 2000 mg/day. In some aspects, choline can be administered in amounts of about 100 mg/day to about 1000 mg/day, or even about 180 mg/day to about 700 mg/day. In other embodiments, the choline can be present in the food composition is an amount ranging from about 100 mg/kg to about 6000 mg/kg, about 1000 mg/kg to about 4000 mg/kg, or even about 2000 mg/kg to about 3000 mg/kg. Additionally, choline can be calculated as an amount of the brain development blend. As such, choline can be present in the brain development blend in an amount from about 50 g/kg to about 400 g/kg, about 100 g/kg to about 350 g/kg, or even about 200 g/kg to about 300 g/kg. As a percentage, the choline can be present as part of the brain development blend in an amount from about 5% to about 40%, about 10% to about 35%, or even about 20% to about 30%.

Generally, thiamine can be present in the food composition in an amount to provide a daily dose from about 0.1 mg/day to about 50 mg/day. In some aspects, thiamine can be administered in amounts of about 0.5 mg/day to about 25 mg/day, or even about 1.5 mg/day to about 12.5 mg/day. In other embodiments, the thiamine can be present in the food composition is an amount ranging from about 1 mg/kg to about 150 mg/kg, about 10 mg/kg to about 100 mg/kg, or even about 30 mg/kg to about 80 mg/kg. Additionally, thiamine can be calculated as an amount of the brain development blend. As such, thiamine can be present in the brain development blend in an amount from about 0.1 g/kg to about 50 g/kg, about 0.5 g/kg to about 20 g/kg, or even about 1 g/kg to about 10 g/kg. As a percentage, the thiamine can be present as part of the brain development blend in an amount from about 0.01% to about 5%, about 0.05% to about 2%, or even about 0.1% to about 1%.

Generally, riboflavin can be present in the food composition in an amount to provide a daily dose from about 0.1 mg/day to about 50 mg/day. In some aspects, riboflavin can be administered in amounts of about 0.5 mg/day to about 25 mg/day, or even about 1.5 mg/day to about 10 mg/day. In other embodiments, the riboflavin can be present in the food composition is an amount ranging from about 1 mg/kg to about 100 mg/kg, about 10 mg/kg to about 50 mg/kg, or even about 10 mg/kg to about 30 mg/kg. Additionally, riboflavin can be calculated as an amount of the brain development blend. As such, riboflavin can be present in the brain development blend in an amount from about 0.1 g/kg to about 50 g/kg, about 0.5 g/kg to about 20 g/kg, or even about 1 g/kg to about 10 g/kg. As a percentage, the riboflavin can be present as part of the brain development blend in an amount from about 0.01% to about 5%, about 0.05% to about 2%, or even about 0.1% to about 1%.

Generally, pantothenic acid can be present in the food composition in an amount to provide a daily dose from about 0.1 mg/day to about 100 mg/day. In some aspects, pantothenic acid can be administered in amounts of about 0.5 mg/day to about 50 mg/day, or even about 1.5 mg/day to about 25 mg/day. In other embodiments, the pantothenic acid can be present in the food composition is an amount ranging from about 1 mg/kg to about 250 mg/kg, about 10 mg/kg to about 100 mg/kg, or even about 25 mg/kg to about 75 mg/kg. Additionally, pantothenic acid can be calculated as an amount of the brain development blend. As such, pantothenic acid can be present in the brain development blend in an amount from about 0.1 g/kg to about 50 g/kg, about 0.5 g/kg to about 20 g/kg, or even about 1 g/kg to about 10 g/kg. As a percentage, the pantothenic acid can be present as part of the brain development blend in an amount from about 0.01% to about 5%, about 0.05% to about 2%, or even about 0.1% to about 1%.

Generally, niacin can be present in the food composition in an amount to provide a daily dose from about 0.1 mg/day to about 250 mg/day. In some aspects, niacin can be administered in amounts of about 1 mg/day to about 150 mg/day, or even about 10 mg/day to about 50 mg/day. In other embodiments, the niacin can be present in the food composition is an amount ranging from about 1 mg/kg to about 600 mg/kg, about 10 mg/kg to about 400 mg/kg, or even about 100 mg/kg to about 300 mg/kg. Additionally, niacin can be calculated as an amount of the brain development blend. As such, niacin can be present in the brain development blend in an amount from about 1 g/kg to about 50 g/kg, about 10 g/kg to about 30 g/kg, or even about 15 g/kg to about 25 g/kg. As a percentage, the niacin can be present as part of the brain development blend in an amount from about 0.1% to about 5%, about 1% to about 3%, or even about 1.5% to about 2.5%.

Generally, pyridoxine can be present in the food composition in an amount to provide a daily dose from about 0.1 mg/day to about 50 mg/day. In some aspects, pyridoxine can be administered in amounts of about 0.5 mg/day to about 20 mg/day, or even about 1 mg/day to about 10 mg/day. In other embodiments, the pyridoxine can be present in the food composition is an amount ranging from about 1 mg/kg to about 100 mg/kg, about 10 mg/kg to about 40 mg/kg, or even about 10 mg/kg to about 20 mg/kg. Additionally, pyridoxine can be calculated as an amount of the brain development blend. As such, pyridoxine can be present in the brain development blend in an amount from about 0.1 g/kg to about 50 g/kg, about 0.5 g/kg to about 20 g/kg, or even about 1 g/kg to about 10 g/kg. As a percentage, the pyridoxine can be present as part of the brain development blend in an amount from about 0.01% to about 5%, about 0.05% to about 2%, or even about 0.1% to about 1%.

Generally, vitamin B12 can be present in the food composition in an amount to provide a daily dose from about 0.1 μg/day to about 1000 μg/day. In some aspects, vitamin B12 can be administered in amounts of about 1 μg/day to about 150 μg/day, or even about 2 μg/day to about 100 μg/day. In other embodiments, the vitamin B12 can be present in the food composition is an amount ranging from about 0.01 mg/kg to about 5 mg/kg, about 0.05 mg/kg to about 2.5 mg/kg, or even about 0.1 mg/kg to about 1 mg/kg. Additionally, vitamin B12 can be calculated as an amount of the brain development blend. As such, vitamin B12 can be present in the brain development blend in an amount from about 0.001 g/kg to about 10 g/kg, about 0.005 g/kg to about 1 g/kg, or even about 0.01 g/kg to about 0.1 g/kg. As a percentage, the vitamin B12 can be present as part of the brain development blend in an amount from about 0.0001% to about 1%, about 0.0005% to about 0.1%, or even about 0.001% to about 0.01%.

Generally, folic acid can be present in the food composition in an amount to provide a daily dose from about 0.01 mg/day to about 15 mg/day. In some aspects, folic acid can be administered in amounts of about 0.1 mg/day to about 10 mg/day, or even about 0.2 mg/day to about 5 mg/day. In other embodiments, the folic acid can be present in the food composition is an amount ranging from about 0.1 mg/kg to about 50 mg/kg, about 0.5 mg/kg to about 20 mg/kg, or even about 1 mg/kg to about 10 mg/kg. Additionally, folic acid can be calculated as an amount of the brain development blend. As such, folic acid can be present in the brain development blend in an amount from about 0.01 g/kg to about 10 g/kg, about 0.05 g/kg to about 5 g/kg, or even about 0.1 g/kg to about 1 g/kg. As a percentage, the folic acid can be present as part of the brain development blend in an amount from about 0.001% to about 1%, about 0.005% to about 0.5%, or even about 0.01% to about 0.1%.

Generally, vitamin E can be present in the food composition in an amount to provide a daily dose from about 0.1 mg/day to about 500 mg/day. In some aspects, vitamin E can be administered in amounts of about 0.25 mg/day to about 250 mg/day, or even about 0.5 mg/day to about 150 mg/day. In other embodiments, the vitamin E can be present in the food composition is an amount ranging from about 1 mg/kg to about 3000 mg/kg, about 10 mg/kg to about 2000 mg/kg, or even about 100 mg/kg to about 1000 mg/kg. Additionally, vitamin E can be calculated as an amount of the brain development blend. As such, vitamin E can be present in the brain development blend in an amount from about 1 g/kg to about 250 g/kg, about 5 g/kg to about 150 g/kg, or even about 10 g/kg to about 100 g/kg. As a percentage, the vitamin E can be present as part of the brain development blend in an amount from about 0.1% to about 25%, about 0.5% to about 15%, or even about 1% to about 10%.

Generally, vitamin C can be present in the food composition in an amount to provide a daily dose from about 0.1 mg/day to about 8000 mg/day. In some aspects, vitamin C can be administered in amounts of about 0.5 mg/day to about 4000 mg/day, or even about 1 mg/day to about 2000 mg/day. In other embodiments, the vitamin C can be present in the food composition is an amount ranging from about 1 mg/kg to about 5000 mg/kg, about 10 mg/kg to about 3000 mg/kg, or even about 100 mg/kg to about 1000 mg/kg. Additionally, vitamin C can be calculated as an amount of the brain development blend. As such, vitamin C can be present in the brain development blend in an amount from about 1 g/kg to about 250 g/kg, about 5 g/kg to about 150 g/kg, or even about 10 g/kg to about 100 g/kg. As a percentage, the vitamin C can be present as part of the brain development blend in an amount from about 0.1% to about 25%, about 0.5% to about 15%, or even about 1% to about 10%.

In some embodiments, the present compositions can comprise a protein. The protein can be crude protein material and may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include beef, pork, lamb, equine, poultry, fish, and mixtures thereof. In one embodiment, the food compositions can comprises the protein in amounts from about 5%, 10%, 15%, 20%, 25%, 30%, 35%, 40%, 45%, 50%, 55%, or even 60% to about 25%, 30%, 35%, 40%, 45%, 50%, 55%, 60%, 65%, or even 70%, including various subranges within these amounts. In one aspect, the protein can be from about 30% to about 55% of the food composition.

In some embodiments, the present compositions can comprise carbohydrates. Generally, any type of carbohydrate can be used in the food compositions. Examples of suitable carbohydrates include grains or cereals such as rice, corn, millet, sorghum, alfalfa, barley, soybeans, canola, oats, wheat, rye, triticale and mixtures thereof. The compositions may also optionally comprise other materials such as dried whey and other dairy by-products. In one embodiment, the carbohydrate comprises from about 5% to about 10% of the food composition. In another embodiment, the carbohydrate comprises from about 10% to about 15% of the food compositions. In other aspects, the carbohydrate can be present in amounts from about 5%, 10%, 15%, 20%, 25%, 30%, 35%, or even 40% to about 10%, 15%, 20%, 25%, 30%, 35%, 40%, 45%, or even 50%.

In some embodiments, the food compositions can include fat. Examples of suitable fats include animal fats and vegetable fats. In one aspect, the fat source can be an animal fat source such as tallow or poultry fat. Vegetable oils such as corn oil, sunflower oil, safflower oil, grape seed oil, soy bean oil, olive oil and other oils rich in monounsaturated and polyunsaturated fatty acids, may also be used. In one embodiment, the food compositions can comprises the fat in amounts from about 5%, 10%, 15%, 20%, 25%, 30%, or even 35% to about 10%, 15%, 20%, 25%, 30%, 35%, or even 40%, including various subranges within these amounts. In one aspect, the fat comprises from about 25% to about 35% of the food composition.

The administration can be performed on as-needed basis, an as-desired basis, a regular basis, or intermittent basis. In one aspect, the food composition can be administered to the animal on a regular basis. In one aspect, at least weekly administration can be performed. More frequent administration or consumption, such as twice or three times weekly, can be performed in certain embodiments. In one aspect, an administration regimen can comprise at least once daily consumption.

According to the presently described methods, administration, including administration as part of a dietary regimen, can span a period ranging from parturition until the adult life of the animal. In various embodiments, the animal can be a human or companion animal such as a dog or cat. Generally, the animal can be a young or growing animal. In other embodiments, administration can begin, for example, on a regular or extended regular basis lasting for weeks, months, or years.

Such administration can be performed for a time required to accomplish one or more objectives described herein, e.g., increased trainability, increased episodic learning, increased episodic memory, reduced spherical aberration of the eye, or enhanced photopic vision, in an animal. Other administration amounts may be appropriate and can be determined based on the animal's initial weight as well as other variables such as species, gender, breed, age, desired health benefit, etc.

The moisture content for such food compositions varies depending on the nature of the food composition. The food compositions may be dry compositions (e.g., kibble), semimoist compositions, wet compositions, or any mixture thereof. In one embodiment, the composition can be a pet food composition, and in one aspect, can be a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one embodiment, the compositions can have moisture content from about 5% to about 20%. Dry food products include a variety of foods of various moisture contents, such that they are relatively shelf-stable and resistant to microbial or fungal deterioration or contamination. Also, in one aspect, dry food compositions can be extruded food products for either humans or companion animals.

The food compositions may also comprise one or more fiber sources. The term "fiber" includes all sources of "bulk" in the food whether digestible or indigestible, soluble or insoluble, fermentable or nonfermentable. Such fibers can be from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefits described herein or to the immune system of an animal.

In some embodiments, the ash content of the food composition ranges from less than 1% to about 15%. In one aspect, the ash content can be from about 5% to about 10%.

Generally, the food composition can be suitable for consumption by an animal, including humans and companion animals such as dogs and cats, as a meal, component of a meal, a snack, supplement, or a treat. Such compositions can include complete foods intended to supply the necessary dietary requirements for an animal. Examples of such food compositions include but are not limited to dry foods, wet foods, drinks, bars, frozen prepared foods, shelf prepared foods, and refrigerated prepared foods.

As discussed herein, the present food compositions may be administered to an animal alone as a complete nutritionally balanced diet, as a supplement, or in conjunction with dietary supplements, vitamins and/or other nutritionally beneficial agents familiar to one of skill in the art, as part of an overall wellness program for the animal. Compositions of the invention may also be useful as a veterinary therapeutic product. As such, the compositions may optionally contain a carrier, diluent, or an excipient, the suitability of which for the intended use being familiar to one of skill in the art.

Food compositions may further comprise one or more substances such as vitamins, minerals, antioxidants, probiotics, prebiotics, salts, and functional additives such as palatants, colorants, emulsifiers, and antimicrobial or other preservatives. Minerals that may be useful in such compositions include, for example, calcium, phosphorous, potassium, sodium, iron, chloride, boron, copper, zinc, magnesium, manganese, iodine, selenium, and the like. Examples of additional vitamins useful herein include such fat soluble vitamins as A, D, E, and K. Inulin, amino acids, enzymes, coenzymes, and the like may be useful to include in various embodiments.

In various embodiments, the food compositions contain at least one of (1) one or more probiotics; (2) one or more inactivated probiotics; (3) one or more components of inactivated probiotics that promote health benefits similar to or the same as the probiotics, e.g., proteins, lipids, glycoproteins, and the like; (4) one or more prebiotics; and (5) combinations thereof. The probiotics or their components can be integrated into the food compositions (e.g., uniformly or non-uniformly distributed in the compositions) or applied to the food compositions (e.g., topically applied with or without a carrier). Such methods are known to skilled artisans, e.g., U.S. Pat. No. 5,968,569 and related patents.

Typical probiotics include, but are not limited to, probiotic strains selected from *Lactobacilli, Bifidobacteria,* or *Enterococci,* e.g., *Lactobacillus reuteii, Lactobacillus acidophilus, Lactobacillus animalis, Lactobacillus ruminis, Lactobacillus johnsonii, Lactobacillus casei, Lactobacillus paracasei, Lactobacillus rhamnosus, Lactobacillus fermentum,* and *Bifidobacterium* sp., *Enterococcus faecium* and *Enterococcus* sp. In some embodiments, the probiotic strain can be selected from the group consisting of *Lactobacillus reuteri* (NCC2581; CNCM 1-2448), *Lactobacillus reuteri* (NCC2592; CNCM 1-2450), *Lactobacillus rhamnosus* (NCC2583; CNCM 1-2449), *Lactobacillus reuteri* (NCC2603; CNCM I-2451), *Lactobacillus reuteri* (NCC2613; CNCM 1-2452), *Lactobacillus acidophilus* (NCC2628; CNCM 1-2453), *Bifidobacterium adolescentis* (e.g., NCC2627), *Bifidobacterium* sp. NCC2657 or *Enterococcus faecium* SF68 (NCIMB 10415). Generally, the food compositions can contain probiotics in amounts sufficient to supply from about $10^4$ to about $10^{12}$ cfu/animal/day, in one aspect, from $10^5$ to about $10^{11}$ cfu/animal/day, and in one specific aspect, from $10^7$ to $10^{10}$ cfu/animal/day. When the probiotics are killed or inactivated, the amount of killed or inactivated probiotics or their components should produce a similar beneficial effect as the live microorganisms. Many such probiotics and their benefits are known to skilled artisans, e.g., EP1213970B1, EP1143806B1, U.S. Pat. No. 7,189,390, EP1482811B1, EP1296565B1, and U.S. Pat. No. 6,929,793. In one embodiment, the probiotic can be *Enterococcus faecium* SF68 (NCIMB 10415). In another embodiment, the probiotics can be encapsulated in a carrier using methods and materials known to skilled artisans.

As stated, the food compositions may contain one or more prebiotics, e.g., fructo-oligosaccharides, gluco-oligosaccharides, galacto-oligosaccharides, isomalto-oligosaccharides, xylo-oligosaccharides, soybean oligosaccharides, lactosucrose, lactulose, and isomaltulose. In one embodiment, the prebiotic can be chicory root, chicory root extract, inulin, or combinations thereof. Generally, prebiotics can be administered in amounts sufficient to positively stimulate the healthy microflora in the gut and cause these "good" bacteria to reproduce. Typical amounts range from about one to about 10 grams per serving or from about 5% to about 40% of the recommended daily dietary fiber for an animal. The probiotics and prebiotics can be made part of the composition by any suitable means. Generally, the agents can be mixed with the composition or applied to the surface of the composition, e.g., by sprinkling or spraying. When the agents are part of a kit, the agents can be admixed with other materials or in their own package. Typically, the food composition contains from about 0.1 to about 10% prebiotic, in one aspect, from about 0.3 to about 7%, and in one specific aspect, from about 0.5 to 5%, on a dry matter basis. The prebiotics can be integrated into the compositions using methods known to skilled artisans, e.g., U.S. Pat. No. 5,952,033.

A skilled artisan can determine the appropriate amount of food ingredients, vitamins, minerals, probiotics, prebiotics, antioxidants, or other ingredients to be used to make a particular composition to be administered to a particular animal. Such artisan can consider the animal's species, age, size, weight, health, and the like in determining how best to formulate a particular composition comprising such ingredients. Other factors that may be considered include the desired dosage of each component, the average consumption of specific types of compositions by different animals (e.g., based on species, body weight, activity/energy demands, and the like), and the manufacturing requirements for the composition.

In a further aspect, the present disclosure provides kits suitable for administering food compositions to animals. The kits comprise in separate containers in a single package or in separate containers in a virtual package, as appropriate for the kit component, one or more of (1) one or more ingredients suitable for consumption by an animal; (2) instructions for how to combine the ingredients and other kit components to produce a composition useful for providing a health benefit as described herein; (3) instructions for how to use the food composition to obtain such benefits; (4) optionally, one or more probiotics; (5) optionally, one or more inactivated probiotics; (6) optionally, one or more components of inactivated probiotics that promote health benefits similar to or the same as the probiotics, e.g., proteins, lipids, glycoproteins, and the like; (7) optionally, one or more prebiotics; (8) a device for preparing or combining the kit components to produce a composition suitable for administration to an animal; and (9) a device for administering the combined or prepared kit components to an animal. In one embodiment, the kit comprises one or more ingredients suitable for consumption by an animal. In another embodiment, the kit comprises instructions for how to combine the ingredients to produce a composition useful for obtaining a health benefit as described herein.

When the kit comprises a virtual package, the kit is limited to instructions in a virtual environment in combination with one or more physical kit components. The kit contains components in amounts sufficient for to obtain a health benefit as described herein. Typically, the kit components can be admixed just prior to consumption by an animal. The kits may contain the kit components in any of various combinations and/or mixtures. In one embodiment, the kit contains a container of food for consumption by an animal. The kit may contain additional items such as a device for mixing ingredients or a device for containing the admixture, e.g., a food bowl. In another embodiment, the food compositions can be mixed with additional nutritional supplements such as vitamins and minerals that promote good health in an animal. The components can be each provided in separate containers in a single package or in mixtures of various components in different packages. In some embodiments, the kits comprise one or more other ingredients suitable for consumption by an animal. In one aspect, such kits can comprise instructions describing how to combine the ingredients to form a food composition for consumption by the animal, generally by mixing the ingredients or by applying optional additives to the other ingredients, e.g., by sprinkling nutritional supplements on a food composition.

In a further aspect, a means for communicating information about or instructions for one or more of (1) using a food composition for obtaining one of the health benefits described herein; (2) contact information for consumers to use if they have a question regarding the methods and compositions described herein; and (3) nutritional information about the food composition can be provided. The communication means can be useful for instructing on the benefits of using the present methods or compositions and communicating the approved methods for administering food compositions to an animal. The means comprises one or more of a physical or electronic document, digital storage media, optical storage media, audio presentation, audiovisual display, or visual display containing the information or instructions. In one aspect, the means can be selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In another aspect, methods for manufacturing a food composition comprising one or more other ingredients suitable for consumption by an animal, e.g., one or more of protein, fat, carbohydrate, fiber, vitamins, minerals, probiotics, prebiotics, and the like, can comprise admixing one or more of the ingredients suitable for consumption by an animal. The composition can be made according to any method suitable in the art.

In another aspect, a package useful for containing compositions described herein can comprise at least one material suitable for containing the food composition and a label affixed to the package containing a word or words, picture, design, acronym, slogan, phrase, or other device, or combination thereof that indicates that the contents of the package contains the food composition. In some embodiments, the label affixed to the package contains a word or words, picture, design, acronym, slogan, phrase, or other device, or combination thereof that indicates that the contents of the package contains the food composition with beneficial properties relating to a health benefit described herein. In one aspect, such device can comprise the words "enhances memory," enhances trainability," "enhances learning," "enhances vision," or an equivalent or similar expression printed on the package. Any package configuration and packaging material suitable for containing the composition can be used herein, e.g., bag, box, bottle, can, pouch, and the like manufactured from paper, plastic, foil, metal, and the like. In one embodiment, the package contains a food composition adapted for a particular animal such as a human, canine, or feline, as appropriate for the label, in one aspect, a companion animal food composition for dogs or cats. In one embodiment, the package can be a can or pouch comprising a food composition described herein. In various embodiments, the package further comprises at least one window that permit the package contents to be viewed without opening the package. In some embodiments, the window can be a transparent portion of the packaging material. In others, the window can be a missing portion of the packaging material.

EXAMPLES

The invention can be further illustrated by the following example, although it will be understood that this example is included merely for purposes of illustration and is not intended to limit the scope of the invention unless otherwise specifically indicated.

Example 1—Puppy Study

At baseline, puppies of 2.5 months of age were randomized into two groups, and each group had 16 puppies with equal gender distribution. During the feeding study, puppies were fed either a test diet containing a brain development blend (BDB) with elevated levels of B vitamins, taurine, choline, antioxidants (VE and VC), and omega-3 polyunsaturated fatty acids (PUFAs) (specifically, docosahexaenoic acid (DHA) and eicosapentaenoic acid (EPA)) or a control diet (Table 1) for 13 months. The control diet was a complete and balanced diet containing the essential nutrients included in the BDB at levels above AAFCO minimal requirements (Table 1). Several cognitive tests were given to the puppies during the feeding study.

TABLE 1

| Nutrient | AAFCO min (dry matter) | Control (dry matter) | BDB (dry matter) |
|---|---|---|---|
| DHA (mg/kg) | 250* | 250 | 2000 |
| EPA (mg/kg) | 250* | 250 | 2000 |
| Taurine (mg/kg) | N/A** | 769 | 2237 |
| Choline (mg/kg) | 1360 | 1900 | 2689 |
| Thiamine (mg/kg) | 2.25 | 12.8 | 48.8 |
| Riboflavin (mg/kg) | 5.2 | 11.1 | 22.9 |
| Pantothenic acid (mg/kg) | 12 | 20 | 56 |
| Niacin (mg/kg) | 13.6 | 85 | 189 |
| Pyridoxine (mg/kg) | 1.5 | 6.1 | 16.7 |
| Folic acid (mg/kg) | 0.216 | 2.1 | 6.4 |
| B12 (mg/kg) | 0.028 | 0.055 | 0.124 |
| Vitamin E (IU/kg) | 50 | 90 | 600 |
| Vitamin C (mg/kg) | N/A** | 0 | 150 |

* AAFCO does not require individual amounts but a combined 500 of DHA and EPA
**AAFCO does not require this nutrient for puppies The results showed that puppies in both groups performed equally well in common cognitive function tests evaluating learning, working memory, long-term memory, associative learning, visuospatial learning and memory, executive function, confirming that the control diet contain sufficient nutrients to support normal brain and cognitive development. However, puppies fed the test diet had significantly better performance in complex cognitive tests evaluating episodic learning and memory when they were puppies around 6 months of age (DNMP) and the benefits remains when they were 15 months of age (Pattern Separation Test) (Table 2). In addition, variable landmark tests showed that the BDB puppies showed a significantly smaller change at the longest distance (land4, the most difficult of the tests) than the control puppies (Table 2). Higher difference between Land0 (easiest) and Land4 (most difficult) in control puppies than in the BDB puppies indicated that control puppies handled most difficult test (Land4) worse than BDB puppies (Table 2).

TABLE 2

| | Delayed non-matching to position Test (DNMP) (% Correct Responses (%)) | Pattern Separation Test (Errors to Criterion) | Differences in # of Correct Responses in Variable Landmark Test between Land0 and Land4 (Land0-Land4) |
|---|---|---|---|
| Control | 68.9 | 17.38 | 9.38 |
| BDB | 71.7 | 8.75 | 6.77 |
| Ages (days) | 115-178 | 349-378 | 414-427 |

The DNMP test protocol had two components: an episodic learning component and an episodic memory component. The subjects were tested on 12 trials per session, one session per day from Monday to Friday. Initially, dogs were trained on a five second delay between sample and test presentation with a 30 second inter-trial until a two-stage learning criterion was passed or until the end of the testing period. Criteria for the 5 s DNMP followed the following two-stage system: Stage 1: the dog scored ≥90% correct in a single session or ≥80% over two consecutive sessions, or three consecutive scores of 10/12, 8/12, 10/12 in that order.

Stage 2: the dog had a combined score of ≥70% over three consecutive 10 trials sessions.

For the pattern separation task, each subject was tested on three separate spatial problems with two of the three correct locations on the animals left side (4 positions, two cups, object under one cup). Training on the first problem was carried out over the first 15 consecutive trials, problem 2 was assessed over trials 16-30 and problem 3 over trials 31-45 s. The inter-trial interval was 15 seconds, and to achieve the learning criterion, the subjects were required to score 35/45 correct on a single session and also respond correctly on a minimum of 10 trials for each spatial pattern.

For the landmark discrimination task, each subject's visual ability to use allocentric cues (landmarks) to locate a reward was tested. Dogs were initially trained to locate a cue associated with a food reward (Land0). The subject was then trained to choose the location closest to the cue after the cue was moved away from the food reward. Upon completion of a two-stage criterion, the landmark is moved further from the reward in one cm increments (Land1, 2, and 4). Subjects were moved onto the next position after reaching a two-stage criterion at each level, or until the maximum number of sessions was reached.

Subjects were tested at Land0, Land1, and Land4 distances, moving on to the next distance level after meeting the following criteria: Stage 1: the dog scored ≥90% correct in a single session or ≥80% over two consecutive sessions. Stage 2: the dog had a combined score of ≥70% over three consecutive 10 trials sessions.

During the feeding study, the puppies also received several clicker-training tasks to evaluate their real life-like trainability. The Target Tough Training assessed a puppy's trainability involving language comprehension. The trainability test included the following: Test 1—dog touches nose to target object when "touch" cue is given. Test 2—Hold target object in reach of the dog with the dog standing 1 meter in front of the trainer. Dog touches nose to target object when "touch" cue is given. Test 3—hold target object 6 inches above the dog's head, dog rears up to touch nose to target object when "touch" cue is given. Test 4—hold target object in reach of the dog with the dog standing in front of the trainer. Dog touches nose to target object and holds for 2 seconds when the "touch" clue is given. Results are expressed as % of correct responses before passing the task and are given in Table 3.

TABLE 3

| Test | Control | BDB |
| --- | --- | --- |
| Test 1 | 94.8 | 95.8 |
| Test 2 | 88.5 | 91.8 |
| Test 3 | 88.1 | 86.6 |
| Test 4 | 28.1 | 38.6 |

The results showed that the BDB puppies performed better in Test 1 and Test 2, and significantly better than the control puppies in Test 4, which is the most difficult one among the Target Touch training tasks. These results are consistent with the observed better performance by the BDB puppies in complex cognitive tests than the control puppies.

In the specification, there have been disclosed certain embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A method for providing a health benefit to a growing animal, the method comprising administering to the growing animal a food composition, wherein the food composition is administered in an amount to provide:

from about 10 mg/day to about 3000 mg/day docosahexaenoic acid (DHA), from about 10 mg/day to about 3000 mg/day eicosapentaenoic acid (EPA), from about 50 mg/day to about 2000 mg/day taurine, from about 50 mg/day to about 2000 mg/day choline, from about 0.1 mg/day to about 50 mg/day thiamine, from about 0.1 mg/day to about 50 mg/day riboflavin, from about 0.1 mg/day to about 100 mg/day pantothenic acid, from about 0.1 mg/day to about 250 mg/day niacin, from about 0.1 mg/day to about 50 mg/day pyridoxine, from about 0.1 µg/day to about 1000 µg/day vitamin B12, and from about 0.01 mg/day to about 15 mg/day folic acid;

wherein the health benefit is selected from the group consisting of enhanced brain and cognitive development, increased trainability, increased episodic learning, increased episodic memory, reduced spherical aberration of the eye, enhanced photopic vision, and combinations thereof, wherein the food composition consists of protein, carbohydrate, fat, the DHA, the EPA, the taurine, the choline, the thiamine, the riboflavin, the pantothenic acid, the niacin, the pyridoxine, the vitamin B12, the folic acid, and optionally an additional ingredient selected from the group consisting of a mineral, a probiotic, a prebiotic, a salt, a palatant, a colorant, an emulsifier, a preservative, an amino acid, an enzyme, a coenzyme, an additional vitamin, moisture, and combinations thereof, wherein the protein is one or more of corn gluten meal, wheat gluten, cottonseed, or an animal protein.

2. The method of claim 1, wherein the food composition comprises:

from about 15% to about 70% protein, from about 5% to about 50% carbohydrate, from about 5% to about 40% fat, from about 100 mg/kg to about 3000 mg/kg DHA, from about 100 mg/kg to about 3000 mg/kg EPA, from about 100 mg/kg to about 5000 mg/kg taurine, from about 100 mg/kg to about 6000 mg/kg choline, from about 1 mg/kg to about 150 mg/kg thiamine, from about 1 mg/kg to about 100 mg/kg riboflavin, from about 1 mg/kg to about 250 mg/kg pantothenic acid, from about 1 mg/kg to about 600 mg/kg niacin, from about 1 mg/kg to about 100 mg/kg pyridoxine, from about 0.01 mg/kg to about 5 mg/kg vitamin B12, and from about 0.1 mg/kg to about 50 mg/kg folic acid.

3. The method of claim 1, wherein the food composition is a supplement comprising a brain development blend, the brain development blend comprising:

from about 50 g/kg to about 350 g/kg DHA, from about 50 g/kg to about 350 g/kg EPA, from about 50 g/kg to about 350 g/kg taurine, from about 50 g/kg to about 400 g/kg choline, from about 0.1 g/kg to about 50 g/kg thiamine, from about 0.1 g/kg to about 50 g/kg riboflavin, from about 0.1 g/kg to about 50 g/kg pantothenic acid, from about 1 g/kg to about 50 g/kg niacin, from about 0.1 g/kg to about 50 g/kg pyridoxine, from about 0.001 g/kg to about 10 g/kg vitamin B12, and from about 0.01 g/kg to about 10 g/kg folic acid.

4. The method of claim 1, wherein the food composition is administered to the growing animal on a regular basis.

5. The method of claim 1, wherein the food composition is a pet food composition.

6. The method of claim 1, wherein the growing animal is a companion animal.

7. The method of claim 1, wherein the optional additional vitamin includes vitamin E and vitamin C.

8. The method of claim 1, wherein the health benefit is reduced spherical aberration of the eye, enhanced photopic vision, or a combination thereof.

9. The method of claim 1, wherein the health benefit is enhanced brain and cognitive development, increased trainability, increased episodic learning, increased episodic memory, or a combination thereof.

10. The method of claim 1, wherein the growing animal is a canine.

11. The method of claim 1, wherein the amount of the food composition administered to the growing animal provides:

140 mg/day to 500 mg/day DHA, 140 mg/day to 500 mg/day EPA, 150 mg/day to 600 mg/day taurine, 180 mg/day to 700 mg/day choline, 1.5 mg/day to 12.5 mg/day thiamine, 1.5 mg/day to 10 mg/day riboflavin, 1.5 mg/day to 25 mg/day pantothenic acid, 10 mg/day to 50 mg/day niacin, 1 mg/day to 10 mg/day pyridoxine, 2 µg/day to 100 µg/day vitamin B12, and 0.2 mg/day to 5 mg/day folic acid.

12. The method of claim 11, wherein the growing animal is a canine.

13. The method of claim 1, wherein the animal protein is selected from the group consisting of casein, albumin, meat protein, and mixtures thereof.

14. The method of claim 13, wherein the meat protein is selected from the group consisting of beef, pork, lamb, equine, poultry, fish, and mixtures thereof.

* * * * *